United States Patent
Osaka et al.

(10) Patent No.: US 7,146,229 B2
(45) Date of Patent: Dec. 5, 2006

(54) CONTROLLER FOR AN ANALYZER

(75) Inventors: Naoki Osaka, Kyoto-fu (JP); Tsuyoshi Morikawa, Kyoto-fu (JP); Nobuyuki Tatsumi, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 32 days.

(21) Appl. No.: 11/052,747

(22) Filed: Feb. 9, 2005

(65) Prior Publication Data

US 2005/0193262 A1 Sep. 1, 2005

(30) Foreign Application Priority Data

Feb. 13, 2004 (JP) .............................. 2004-036479

(51) Int. Cl.
*G05B 11/01* (2006.01)
*G05B 19/42* (2006.01)
*G06F 15/177* (2006.01)
*G06F 15/16* (2006.01)

(52) U.S. Cl. .............................. 700/20; 700/19; 700/23; 700/86; 700/87; 709/220; 709/221; 709/246; 345/156; 345/157; 345/158; 436/43; 436/50; 717/124; 717/126; 717/131

(58) Field of Classification Search ............ 700/18–20, 700/23, 86, 87, 88, 180, 181; 714/724, 725, 714/726; 717/100, 110, 123, 124, 126, 131; 709/227, 228, 229, 220–222, 246; 345/156–158; 436/43, 50

See application file for complete search history.

(56) References Cited

U.S. PATENT DOCUMENTS

| | | | |
|---|---|---|---|
| 4,812,820 A | 3/1989 | Chatwin | |
| 5,410,471 A * | 4/1995 | Alyfuku et al. ............. | 600/300 |
| 5,695,718 A | 12/1997 | Imai et al. | |
| 5,754,426 A | 5/1998 | Dumais | |
| 5,970,425 A | 10/1999 | Ono et al. | |
| 6,198,482 B1 | 3/2001 | Okada | |
| 6,252,846 B1 * | 6/2001 | Fujita ........................ | 370/220 |
| 6,263,347 B1 | 7/2001 | Kobayashi et al. | |
| 6,748,321 B1 * | 6/2004 | Watanabe et al. ........... | 701/209 |
| 2002/0083459 A1 * | 6/2002 | Kondo et al. ................. | 725/88 |
| 2002/0184326 A1 | 12/2002 | Thomson | |
| 2002/0188565 A1 * | 12/2002 | Nakamura et al. ............ | 705/42 |
| 2003/0188255 A1 * | 10/2003 | Shimizu et al. .......... | 715/501.1 |
| 2003/0229475 A1 | 12/2003 | Osaka et al. | |

(Continued)

FOREIGN PATENT DOCUMENTS

JP 04-313933 11/1992

(Continued)

Primary Examiner—Ramesh Patel
(74) Attorney, Agent, or Firm—Westerman, Hattori, Daniels & Adrian, LLP.

(57) ABSTRACT

A built-in analyzer controller including: a device controlling circuit for controlling the hardware of an analyzer; a network interface circuit for connecting the analyzer to a network; and built-in programs including a server program for performing a communication through the network interface using a predetermined communication protocol between the analyzer and an external terminal. The server program performs the processes of: sending information of the operating status of the analyzer to the external terminal on receiving a request for the same from the external terminal; and setting a control parameter of the analyzer using the device controlling circuit on receiving a request for setting the control parameter from the external terminal. Using the analyzer controller, the user can monitor and control an analyzer or analyzers connected to a LAN from a remote place, without requiring special programs, and at low cost.

5 Claims, 3 Drawing Sheets

U.S. PATENT DOCUMENTS

2004/0098148 A1    5/2004  Retlich et al.
2004/0208188 A1*  10/2004  Kimura et al. .............. 370/401
2004/0268193 A1*  12/2004  Nishida et al. ............. 714/724

FOREIGN PATENT DOCUMENTS

| JP | 06-112989    | 4/1994  |
| JP | 10-282107    | 10/1998 |
| JP | 11-051942    | 2/1999  |
| JP | 11-142111    | 5/1999  |
| JP | 11-142410    | 5/1999  |
| JP | 11-149431 A  | 6/1999  |
| JP | 2000-283935  | 10/2000 |

* cited by examiner

CONTROLLER FOR AN ANALYZER

The present invention relates to a controller for controlling an analyzer such as a high-performance liquid chromatograph.

BACKGROUND OF THE INVENTION

According to the state of the art, a controller is necessary to use an analyzer such as a liquid chromatograph (LC), which is controlled in one of the following methods.

An independent control unit equipped with firmware (or built-in) programs is prepared, and is connected to the LC with a communication cable.

Appropriate LC controlling programs are installed in a general-purpose computer such as a personal computer, which constitutes an LC controller, and the computer is connected to the LC with a communication cable.

An independent control unit is expensive due to the high cost of manufacture. And the control programs installed as firmware in the control units, in general, differ from one type of analyzer to another. When, therefore, the firmware programs are to be newly developed or to be modified, detailed information specific to that type of analyzer is necessary, which is burdensome to the program developers.

In the case of installing controlling programs in a general-purpose computer, the programs normally include, besides those for controlling the LC analyzer, a group of programs for analyzing and processing data obtained through measurements. This means that the controlling programs as a whole become quite versatile and very big, so that the development and modification of the programs also require a lot of time and cost.

From the users' point of view, a certain level of knowledge or experience is needed to master such versatile programs, and the acquisition of such knowledge or experience takes a lot of time. On the other hand, many users actually use the programs only for formulaic tasks, such as monitoring the operation of the analyzer. For such tasks, it will be more convenient to use one simple program rather than several versatile programs. In this sense, conventional controlling programs need reconsidering.

Independent control units have no such problem. But the user must go to the control unit when the user wants to monitor the operation of the analyzer or set/reset the analyzing conditions, which requires additional time. Many types of analyzers have been proposed so far which are equipped with a controller enabling the user to monitor the operation of the analyzer from a remote place. The Japanese Unexamined Patent Publication No. 2000-283935 discloses one such analyzer. But until now there has never been an analyzer that allows the user to set/reset the analyzing condition from a remote place.

SUMMARY OF THE INVENTION

One of the objects of the present invention is therefore to provide a controller for an analyzer that is easy to operate, convenient, and which allows the user to monitor or control the analyzer from a remote place, without requiring special programs, and at low cost.

According to the present invention, a controller for an analyzer built in the controller includes:

a device controlling circuit for controlling the analyzer;
a network interface circuit for connecting the analyzer to a network; and
built-in programs including a server program for performing a communication through the network interface using a predetermined communication protocol between the analyzer and an external terminal,
wherein the server program performs processes of
sending information of the operating status of the analyzer to the external terminal on receiving a request for the same from the external terminal, and
setting a control parameter of the analyzer using the device controlling circuit on receiving a request for setting the control parameter from the external terminal.

In the analyzer controller described above, the network interface circuit may be one that conforms to the Ethernet (trademark) standard (IEEE802.3).

In the analyzer controller described above, the server program may perform the communication using the HTTP protocol.

In the analyzer controller described above, the built-in programs may further include a control program for controlling an operation of the analyzer using the device controlling circuit, and the server program may obtain the operating status information from the control program, and set a new value of the control parameter to the device controlling circuit using the control program.

In the analyzer controller described above, the built-in programs may further include an inter-controller communication program for enabling the analyzer controller to share the operating status information with another analyzer controller connected to the network. Examples of the operating status information are: the grouping structure (or the domain structure) of the analyzers on the network, control parameters necessary to synchronize or cooperate plural analyzer on the network, etc.

The analyzer controllers according to the present invention can be manufactured at a lower cost than the independent control units or personal computers with pre-installed control programs. Since the analyzer controller of the present invention is made particularly for monitoring the analyzer or in setting/resetting analyzing conditions, the structure is simple and easy to use, so that learning the operation is also easy.

If the network interface circuit of the analyzer controller of the present invention conforms to the Ethernet standard, the analyzer controller can be hooked to those networks commonly used as LAN (local area network), so that a personal computer connected to the LAN can be used as the above-described external terminal.

If it is constructed in the present invention that the server program performs the communication using the HTTP protocol, web browsers normally installed in personal computers can be used as the client application program for showing the information of the analyzer or for setting parameters of the analyzer. This renders a special program in the user terminal (the external terminal) unnecessary.

If the built-in programs further include the above-described control program, the server program independent of the control program can be easily updated with its operation setting files. This facilitates customizing the information shown on the terminal and parameter settings.

If the built-in programs further include the above-described inter-controller communication program, the information about setting or operating analyzers can be exchanged as desired. This enables the user to view a list of all the analyzers 10 included in the same group, to select one of the analyzers 10 in the list, and to see the status view window of the selected analyzer, which will be described later. It also becomes possible to conduct an analysis using plural analyzers synchronizing or cooperating with one another.

DETAILED DESCRIPTION OF A PREFERRED EMBODIMENT

Figure 1:
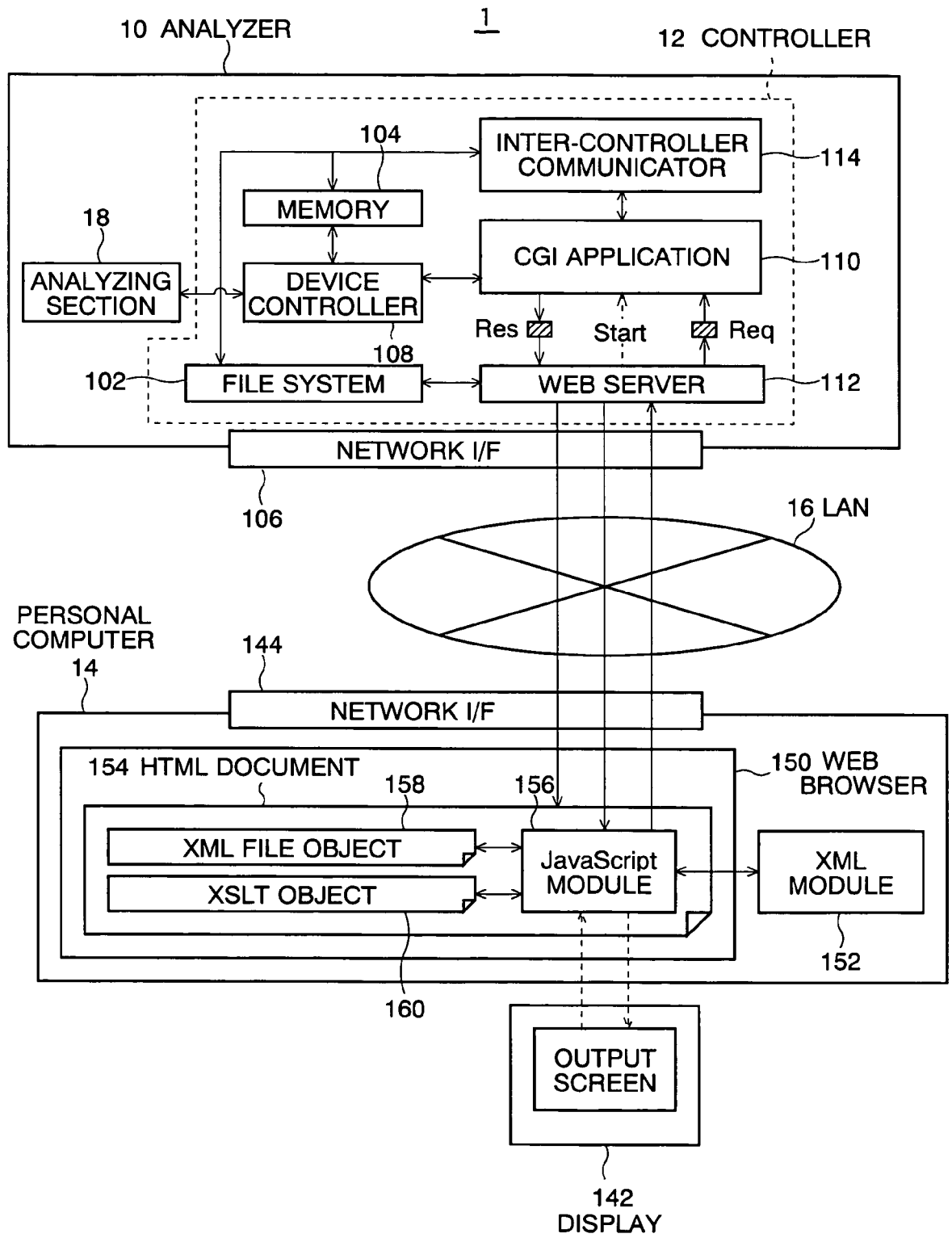
FIG. 1 is a block diagram of an analyzer system using a controller according to the present invention.

An embodiment of the present invention is described referring to FIG. 1, which shows a block diagram of an analyzer system 1 employing an analyzing controller 12 according to the present invention. The system 1 is composed of an analyzer 10, a personal computer 14 and an Ethernet LAN 16.

The analyzer 10 is substantially composed of an analyzing section 18 and the analyzing controller 12, where the analyzing section 18 actually performs an analysis of a sample. In the case of an LC, for example, the analyzing section 18 is composed of a pump, an injector, a column, a detector, and so on. The analyzing controller 12 may be a box type, a board type, a card type or any other type, and is normally built in the analyzer 10 just like an add-in board inserted into an extension slot of a personal computer. The analyzing controller 12 includes a CPU (not shown), a storage device arranged to have an appropriate file system 102, a read/write memory 104, a network interface (I/F) 106, etc.

In the file system 102 of the storage device, programs and data necessary to run the analyzing controller 12 are stored, where the programs include basic programs and library files constituting the operating system (OS) of the analyzing controller 12 and application programs operable on the OS, and the data include those used by the application programs. The application programs include, in the present case, the web server programs, CGI application programs, and script processing programs (JavaScript (Trademark), for example).

In the memory 104, state parameters and control parameters are stored, wherein the state parameters determine the state of the analyzer 10, and the control parameters are used to control the analyzer 10. In the case of an LC, for example, the control parameters include the identification and the injecting amount of a sample selected in an auto-sampler, the flow rate of the liquid carrier in the column, the temperature of the column, and the wavelength of the light used in the detector (in the case of one using a spectrophotometer). The state parameters include, in addition to the control parameters, the lapse time from the start of an analysis, and the indication of the operating state (i.e., "(Analysis) Ready", "(Analysis) Underway", "(Analysis) Halt" or "(Analysis) Finished"), etc.

The network interface 106 conforms to the Ethernet standard (IEEE802.3), and is assigned a unique IP address in the LAN 16.

The controller 12 includes the functional parts of a device controller 108, a CGI application 110, a web server 112 and an inter-controller communicator 114, all of which are constructed by software, i.e., are realized by executing respective appropriate programs. The functions and operations of the functional parts will be described later.

The personal computer 14 includes a CPU (not shown), storage devices (ROM, RAM, hard disk, etc., not shown), input devices (a keyboard, a mouse, etc., not shown), a display device (CRT, LCD, etc.), a network interface (I/F) 144, and other peripheral devices. In the personal computer 14, other than the operating system (not shown), application programs and library programs including a web browser 150 and an XML module 152 are installed. In the web browser 150, the JavaScript execution engine is included. For the XML module 152, the library "MSXML" provided by Microsoft Corporation can be used.

Figure 2:
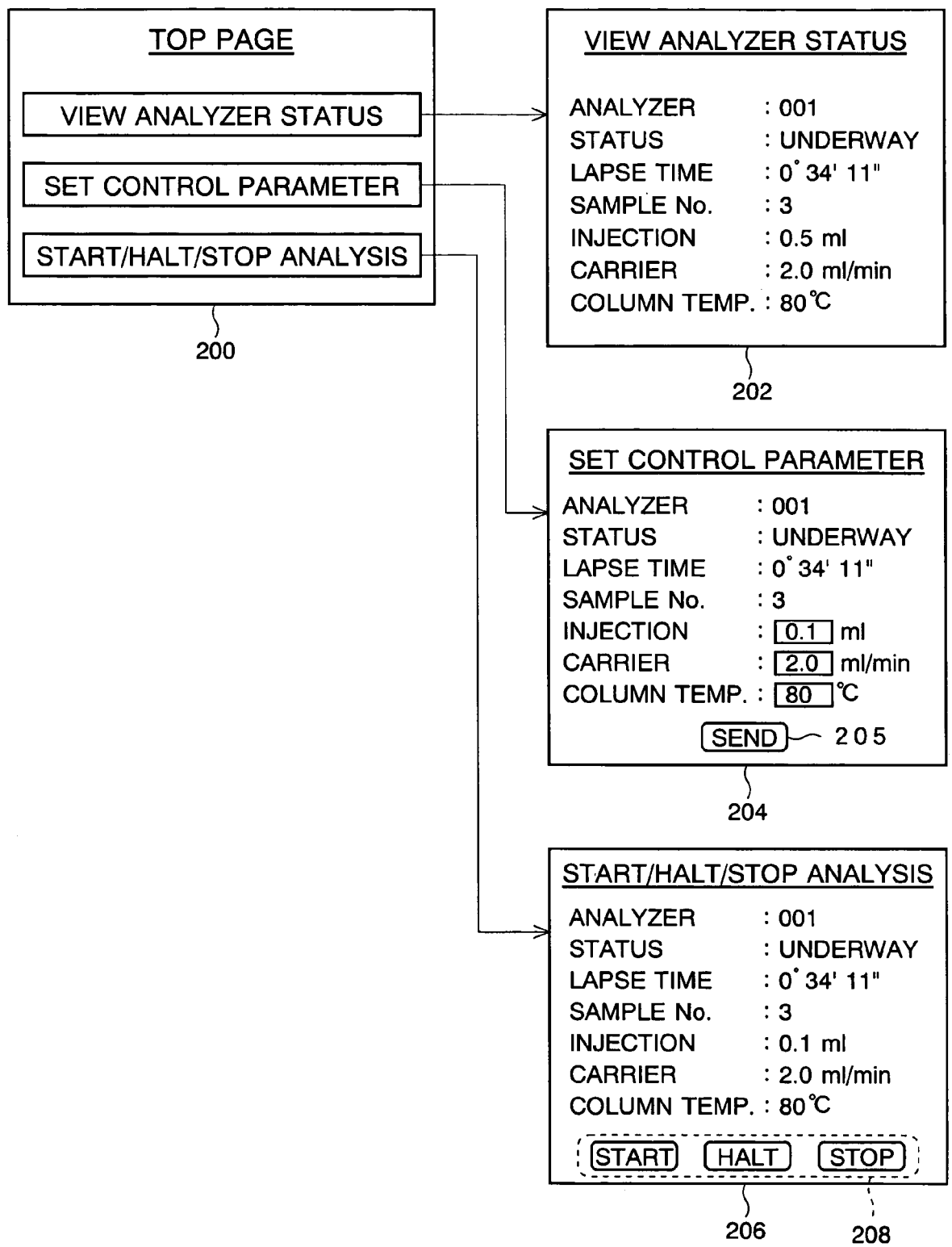
FIG. 2 is a transition diagram of the windows shown on the browser.

When the user activates the web browser 150 and accesses the URL of an object analyzer, the top page of the analyzer appears on the window of the web browser 150. An example of the top page 200 is shown in FIG. 2, in which the following hyperlink menus are tabulated.

VIEW ANALYZER STATUS
SET CONTROL PARAMETERS
START/HALT/STOP ANALYSIS

The confirmation of the status of the analyzer is done as follows.

When the user clicks the "VIEW ANALYZER STATUS" link in the top page 200, the web browser 150 issues a request for acquiring a view status window 202 to the web server 112. Responsive to the request, the web server 112 sends an HTML document 154 (FIG. 1) for showing the view status window 202 to the web browser 150. On receiving the HTML document 154, the web browser 150 executes the JavaScript script embedded in the HTML document 154, and generates a JavaScript module 156. The JavaScript module 156 then issues a request to the web server 112 for acquiring status parameters from the CGI 110.

Responsive to the request, the web server 112 runs an appropriate CGI 110, and passes the request to the CGI 110. On receiving the request, the CGI 110 inquires the status of the analyzer to the device controller 108. Responsive to the inquiry, the device controller 108 reads out status parameters from the memory 104, and sends them to the CGI 110. On receiving the status parameters, the CGI 110 generates an XML file object 158 that describes the names and values of the status parameters in a predetermined format, and sends it to the web server 112. The web server 112 then sends the XML file object 158 and an XSLT object 160 describing the rule for converting the XML file object 158 to an HTML document, to the web browser 150.

In the web browser 150 which has received the XML file object 158, the JavaScript module 156, using the XML module 152, processes the XML file object 158 and the XSLT object 160, and generates HTML codes for constituting the view status window 202 containing the names and values of the status parameters. The web browser 150 reads and analyzes the HTML codes generated by the JavaScript module 156, and shows the view status window 202 on the display 142.

The control parameters of the analyzer are set as follows.

When the user clicks the "SET CONTROL PARAMETERS" link in the top page 200, a parameter setting window 204 including the names and values of control parameters in a predetermined format appears in the web browser 150 (FIG. 2). The process of showing the parameter setting window 204 is almost the same as that of the view status window 202, except that the values of the control parameters are just shown in the view status window 202 while some of them are changeable using an HTML form or input components (i.e., text boxes) in the parameter setting window 204. In order to generate different HTML codes depending on the type of window from the same XML file object 158, the XSLT object 160 should be made to branch the HTML converting processes according to the type of the window.

On the parameter setting window 204, the user puts proper parameters to the input boxes that are inputtable by the user. When the user finishes the input, the user clicks the SEND button 205. Responding to the click, the JavaScript module 156 checks the parameters that have been input by the user, and issues a warning if any of the input values is inappropriate: for example, when a negative value is input into a box for a positive value parameter, or an out-of-limit value is input into a box with an upper and lower limit values.

If the input values are all appropriate, the JavaScript module 156 sends the new values of the parameters to the CGI 110 through the web server 112. Receiving the new values, the CGI 110 sends a command to the device controller 108 to change the control parameters of the analyzer 10 to the new values. The device controller 108 puts the new values to their respective places in the memory 104 corresponding to the control parameters. After that, analyses are conducted using the new values of control parameters.

The "START/HALT/STOP" operation is done as follows.

When the user clicks the "START/HALT/STOP ANALYSIS" link, a status change window 206 appears in the web browser 150 (FIG. 2). The status change window 206 is shown by almost the same process as in the case of the view status window 202, except that three buttons 208, i.e., "START", "HALT" and "STOP" buttons, respectively representing the operation of the start, halt and stop of an analysis, are placed in the status change window 206.

When the user clicks one of the three buttons 208, the JavaScript module 156 checks whether the operation corresponding to the clicked button is practicable to the analyzer at the moment. For example, if the analyzer is in a "STOP" mode, the "HALT" operation or "STOP" operation is unpracticable. In these cases, the JavaScript module 156 issues a message warning that the clicked operation is unpracticable. It is possible, instead, to make unpracticable buttons unclickable, or, further, to fade (or to hide) them on the window, in which case the practicability check is unnecessary.

If the clicked operation is practicable, the JavaScript module 156 sends a request for the clicked operation to the CGI 110 through the web server 112. Responding to the request, the CGI 110 sends a command to the device controller 108 to change the status of the analyzer according to the clicked operation. The device controller 108 then changes the status of the analyzer accordingly.

Figure 3:
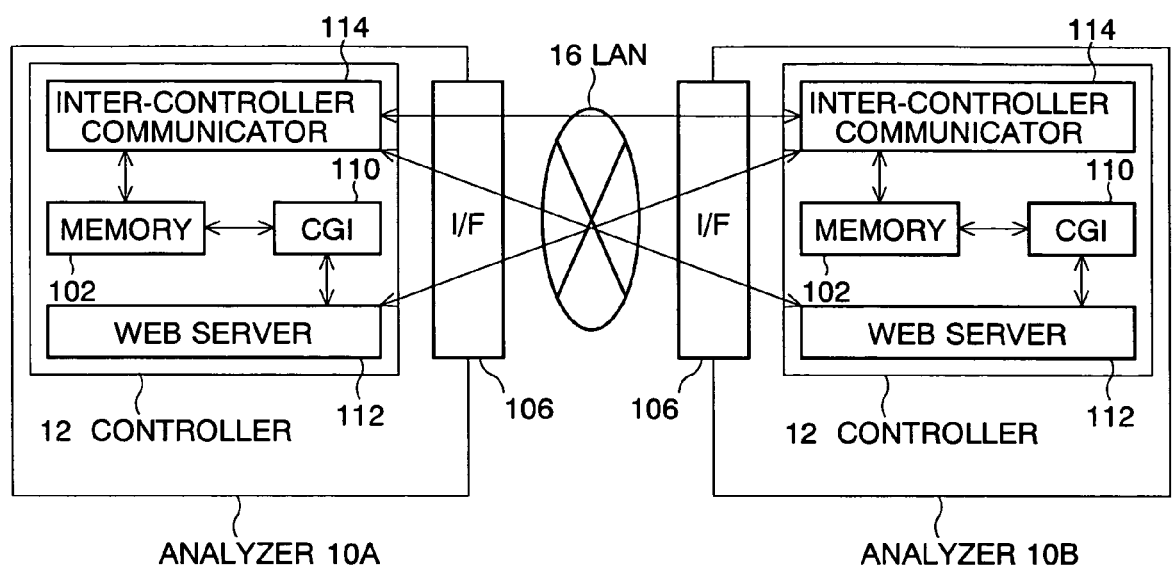
FIG. 3 is a block diagram of a system for exchanging information of setting and operating an analyzer between plural analyzers.

The inter-controller communicator 114 works as follows. When plural analyzers 10A and 10B are connected to a LAN as shown in FIG. 3, the inter-controller communicator 114 of an analyzer 10A can exchange the status and control parameters of the analyzer with those of the other analyzer 10B at any time. This allows the following operation. Using a web browser 150 of a personal computer connected to the LAN 16, the user can access the web server 112 of one of the analyzers 10A connected to the LAN 16, and can see a list of all the analyzers 10 connected to the LAN 16. Selecting one of the analyzers 10 on the list, the user then can see the view status window of the selected analyzer and confirm its current operating status.

Further, the user can conduct an analysis using plural analyzers connected to a LAN 16, linking or synchronizing the analysis operations of the plural analyzers.

Such an inter-controller communication can be one that involves the TCP/IP (Transmission Control Protocol/Internet Protocol) on the web server 112 and CGI 110, or, alternatively, one performed directly between inter-controller communicators 114 using the simpler UDP (User Datagram Protocol).

As explained above, the system of the present embodiment takes full advantage of mostly standard or de facto standard technologies, such as TCP/IP, HTTP, HTML, XML, SXLT, Ethernet, JavaScript, etc. This means that a sophisticated analyzer controlling system can be easily constructed using standard information technologies such as Ethernet LAN, personal computer, web browser, etc., and a controller according to the present invention.

Although only some exemplary embodiments of the present invention have been described in detail above, those skilled in the art will readily appreciate that many modifications are possible without materially departing from the novel teachings and advantages of this invention. Accordingly, all such modifications are intended to be included within the scope of this invention.

What is claimed is:

1. A controller for an analytical instrument built in the analytical instrument, comprising:
    a device controlling circuit for controlling the analytical instrument;
    a network interface circuit for connecting the analytical instrument to a network; and
    built-in programs including a server program for performing a communication through the network interface using a predetermined communication protocol between the analytical instrument and an external terminal,
    wherein the server program performs processes of
    sending information of an operating status of the analytical instrument to the external terminal on receiving a request for the operating status information from the external terminal,
    setting a control parameter of the analytical instrument using the device controlling circuit on receiving a request for setting the control parameter from the external terminal, and
    starting an analysis, halting the analysis and stopping the analysis on receiving a request for start, halt and stop respectively from the external terminal.

2. The controller for an analytical instrument according to claim 1 wherein the network interface circuit conform to the Ethernet standard (IEEE802.3).

3. The controller for an analytical instrument according to claim 1 wherein the server program performs the communication using the HTTP protocol.

4. The controller for an analytical instrument according to claim 1 wherein
    the built-in programs further include a control program for controlling an operation of the analytical instrument using the device controlling circuit, and
    the server program obtains the operating status information from the control program, and sets a new value of the control parameter to the device controlling circuit using the control program.

5. The controller for an analytical instrument according to claim 1 wherein the built-in programs further include an inter-controller communication program for enabling the controller to share the operating status information with another controller connected to the network.

* * * * *